(12) United States Patent
Cardelius

(10) Patent No.: US 6,912,925 B2
(45) Date of Patent: Jul. 5, 2005

(54) ACOUSTIC METER ASSEMBLY

(75) Inventor: Erik Cardelius, Stockholm (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 10/747,635

(22) Filed: Dec. 29, 2003

(65) Prior Publication Data
US 2004/0149039 A1 Aug. 5, 2004

(30) Foreign Application Priority Data
Feb. 5, 2003 (SE) .............................................. 0300290

(51) Int. Cl.$^7$ .......................... G01L 19/14; G01N 29/00
(52) U.S. Cl. ........................................ 73/866.5; 73/570
(58) Field of Search .............................. 73/866.5, 570, 73/24.06, 30.04, 861.28, 861.29, 861.25, 863.71, 61.61, 54.24, 52.25, 61.49, 61.79

(56) References Cited

U.S. PATENT DOCUMENTS

| 5,639,667 | A | * | 6/1997 | Heslot et al. ................ 436/148 |
| 5,814,736 | A | * | 9/1998 | Loschberger et al. ..... 73/861.25 |
| 6,363,773 | B1 | * | 4/2002 | Bowers ...................... 73/24.06 |
| 6,715,339 | B2 | * | 4/2004 | Bonne et al. .............. 73/24.01 |

* cited by examiner

Primary Examiner—Helen Kwok
(74) Attorney, Agent, or Firm—Schiff Hardin LLP

(57) ABSTRACT

An acoustic meter assembly has a measurement chamber for receiving a pressurized fluid to be monitored; an acoustic transducer for transmitting acoustic energy into and receiving the transmitted energy from the measurement chamber; and a holder for the acoustic transducer including a receiving section in which the acoustic transducer is locatable to expose a front surface to fluid pressure within the measurement chamber. The holder further has a pressure transfer arrangement for communicating pressure between the measurement chamber and a rear surface of the transducer, opposite to the front surface.

3 Claims, 1 Drawing Sheet

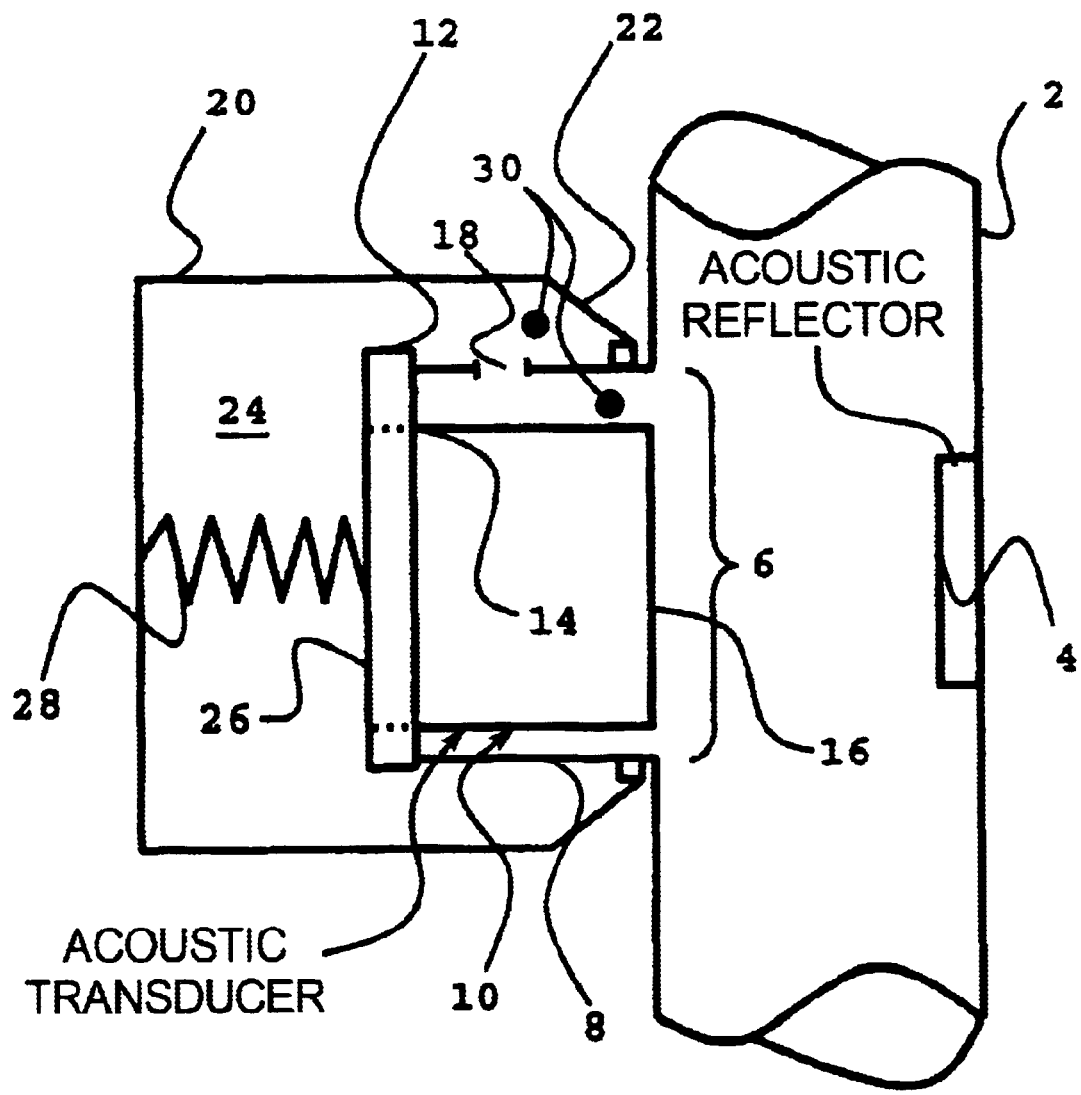

ACOUSTIC METER ASSEMBLY

BACKGROUND OF THE INVENTION

1. Field of the Invention

The present invention relates to an acoustic meter assembly and in particular to a holder for an acoustic transducer employed in such a meter.

2. Description of the Prior Art

Acoustic meters, such as flow meters, gas composition meters, etc. are well known in the art. Such meters typically employ one or more ultrasound acoustic transducers arranged within a measurement chamber for receiving a gas or other fluid, the flow, composition, or other property of which is to be measured. The one or more ultrasound transducers operate to transmit an ultrasound signal into and subsequently receive a dependent ultrasound signal from fluid within the measurement chamber and the flow or other property is determined from differences between the transmitted and the received ultrasound signals. To accomplish this the ultrasound transducer typically is mounted in a holder having a transducer receiving section either connectable to or more usually integrated with an opening in the measurement chamber. A rubber flange is provided which forms a fluid-tight seal between the transducer and the receiving section and acoustically isolates the transducer from the walls of the chamber itself. In this manner a front face of the transducer is exposed to fluid within the chamber.

In order to make accurate determinations using an acoustic meter of the above-described type it is essential that the acoustic path length within the measurement chamber be known accurately. However, the exposed front face of the transducer is subject to any pressure changes of the fluid within the chamber. During inspiration, for example, a transducer employed in the measurement of inspiration gas may be subject to approximately 100 mbar pressure increase at the front surface. Such an increase exerts a pressure force on the front surface that is likely to cause the transducer to move with the rubber flange by approximately 12–13 µm and to thereby increase the acoustic path length by around 25 µm. This increase will lead to an error in the determination made using the meter which will increase the shorter the path within the measurement chamber that is traversed by the acoustic energy becomes. Unfortunately, a short acoustic path, typically of 4 cm or less, is often desirable since this will reduce the gas volume required as well as making any necessary gas temperature measurements easier.

One known solution is to design a holder for the transducer having a biasing element, such as a spring, in contact with a rear face of the transducer. This spring provides a force on the transducer that is counter the force exerted on it by fluid pressure from within the measurement chamber and so inhibits pressure induced movements of the transducer. Unfortunately, a large bias force often has adverse effects on the operation of the transducer and it becomes extremely difficult to provide a bias force that is sufficiently large to prevent the small (micron) movements of the transducer which effect the accuracy at the small acoustic path lengths.

SUMMARY OF THE INVENTION

It is an object of the present invention to alleviate at least some of the aforementioned problems associated with pressure induced movement of the acoustic transducer.

This object is achieved by providing a holder in which fluid pressure is communicated between the opposing front and the rear surfaces of the transducer then the movement of the transducer caused by pressurized fluid in the measurement chamber can be reduced, preferably to zero.

The holder may be formed with a chamber with which the rear surface of the transducer is in pressure communication and with conduits for transferring pressurized fluid between this chamber and the measurement chamber. In this manner pressures at the front and the rear surfaces of the transducer may be simply equilibrated.

DESCRIPTION OF THE DRAWINGS

The single FIGURE is a schematic illustration of a holder located with a measurement chamber of an acoustic meter assembly.

DESCRIPTION OF THE PREFERRED EMBODIMENTS

In the figure a portion of a measurement chamber 2 of an acoustic meter assembly is shown formed with an acoustically reflective surface 4 at least in the region of an opening 6 within an outer wall of the measurement chamber 2. The opening 6 is here formed in permanent connection with an open ended cylindrical transducer receiving section 8 that in the present embodiment extends at right angles from the measurement chamber 2.

An acoustic, typically ultrasound, transducer 10, here illustrated as a single element but may comprise two or more separate acoustic emitters and receivers arranged in one of a number of known measurement configurations, extends into the receiving section 8 and is provided with a deformable, for example rubber, flange 12 that is intended to form a fluid tight seal with an open periphery 14 of the section 8 and helps to locate a front face 16 of the transducer 10 opposite the acoustically reflective surface 4. The front face 16 is thus exposed to fluid within the measurement chamber 2 and when actuated can transmit acoustic energy towards and detect acoustic energy reflected from the surface 4. The section 8 is dimensioned to provide a gap between its inner walls and the outer surface of the transducer 10 through which fluid may flow and is provided with one or more (here one is shown) through holes 18 which, in use, are located in fluid communication with internal the measurement chamber 2.

An end-cap 20 is provided with a mating portion 22 that extends over the transducer receiving section 8 to cover the through holes 18 and locates against the section 8 in a fluid tight connection to form, together with the transducer receiving section 8, a holder for the transducer 10. The end-cap 20, when so located against the section 8, is configured to provide a pressurizing chamber 24 for receiving and, holding fluid with which a rear surface 26 of the transducer 10 will be in pressure communication, here because of exposure of the rear surface 26 to fluid within the pressurizing chamber 24. The end-cap 20 is further configured to cooperate with the through holes 18 and the transducer receiving section 8 to define one or more conduits 30 for the transfer of fluid between the pressurizing chamber 24 and the measurement chamber 2 depending on pressure differences between fluid in the two chambers 2;24. In this manner fluid pressure acting on the front 16 and the rear 24 surfaces of the transducer 10 may be equalized.

In the present embodiment a spring bias 28 is also provided as part of the holder 8,20 to hold the transducer 10 in a correct operating position against vibrations and knocks. The bias force on the transducer 10 that is generated by the spring 28 needs therefore to be much less than would otherwise be required to counter pressure forces that may be generated by pressure changes within fluid in the measurement chamber 2 and the spring 28 may even be omitted.

It will be appreciated by those skilled in the art that, without departing from the inventive concept, a pressure transfer arrangement may be realized in a number of ways to provide for pressure communication between the measurement chamber 2 and the rear surface 26 of the transducer 10 so that pressure forces on the front 16 and the rear 26 surfaces of the transducer 10 are essentially equalized. For example, a piston or a deformable membrane may be arranged to act on the rear surface of the transducer 26 to transfer pressure forces to the rear of the transducer.

Although modifications and changes may be suggested by those skilled in the art, it is the intention of the inventor to embody within the patent warranted hereon all changes and modifications as reasonably and properly come within the scope of his, contribution to the art.

I claim as my invention:

1. In an acoustic meter assembly having a measurement chamber for receiving a pressurized fluid at a fluid pressure to be monitored, and having an acoustic transducer with opposite front and rear surfaces disposed to interact with said pressurized fluid as participation monitoring said fluid pressure, the improvement of a holder for said acoustic transducer comprising:

a receiving station in which said acoustic transducer is locatable to expose said front surface thereof to said fluid pressure in the measurement chamber; and a pressure transfer arrangement for communicating said pressurized fluid from the measurement chamber to the rear surface of the transducer and substantially equalizing said fluid pressure at said front surface and said rear surface of said transducer.

2. A holder as claimed in claim 1 wherein said pressure transfer arrangement comprises a pressurizing chamber in pressure communication with said rear surface of said transducer, and a plurality of conduits for transferring pressurized fluid between the pressurizing chamber and the measurement chamber.

3. A holder as claimed in claim 2 wherein said receiving station comprises a plurality of through holes, and wherein said holder comprises an end cap cooperating with said through holes and said receiving section to define said plurality of conduits and to form said pressurizing chamber.

* * * * *